United States Patent [19]

Beuchat et al.

[11] Patent Number: 5,041,096
[45] Date of Patent: Aug. 20, 1991

[54] FLUID HANDLING METHOD AND SYSTEM AND FLUID INTERFACE APPARATUS USABLE THEREWITH

[75] Inventors: Charles E. Beuchat, Irvine; Harold J. Walbrink, Laguna Niguel, both of Calif.

[73] Assignee: Nestle, S.A., Fort Worth, Tex.

[21] Appl. No.: 427,511

[22] Filed: Oct. 27, 1989

[51] Int. Cl.⁵ .............................................. A61M 1/00
[52] U.S. Cl. .................................. 604/118; 604/119; 417/477
[58] Field of Search .............................. 604/118–120, 604/131, 151, 153, 51, 297; 417/476, 475, 477

[56] References Cited

U.S. PATENT DOCUMENTS

| | | |
|---|---|---|
| 3,690,315 | 9/1972 | Chittenden et al. . |
| 3,723,030 | 3/1973 | Gelfand .................. 417/477 |
| 4,176,746 | 12/1979 | Kooi . |
| 4,218,197 | 8/1980 | Meyer et al. . |
| 4,379,506 | 4/1983 | Davidson . |
| 4,425,115 | 1/1984 | Wuchinich . |
| 4,515,535 | 5/1985 | D'Silva . |
| 4,569,674 | 2/1986 | Phillips et al. . |
| 4,599,055 | 7/1986 | Dykstra . |
| 4,661,093 | 4/1987 | Beck et al. .............. 604/153 |
| 4,784,649 | 11/1988 | Imonti et al. . |
| 4,921,477 | 5/1990 | Davis ...................... 604/119 |

Primary Examiner—Stephen C. Pellegrino
Assistant Examiner—Michael Rafa
Attorney, Agent, or Firm—Lowe, Price, LeBlanc & Becker

[57] ABSTRACT

A fluid handling system is disclosed for use with a surgical handpiece in microsurgery. Included is a fluid interface block apparatus which is structurally adapted to be removably and firmly secured to a control unit of the type which controls the fluidics of a microsurgery system. The system includes a plurality of peristaltic pumps arranged with respect to each other so as to minimize the effects of fluid pressure pulsations produced by each one.

53 Claims, 5 Drawing Sheets

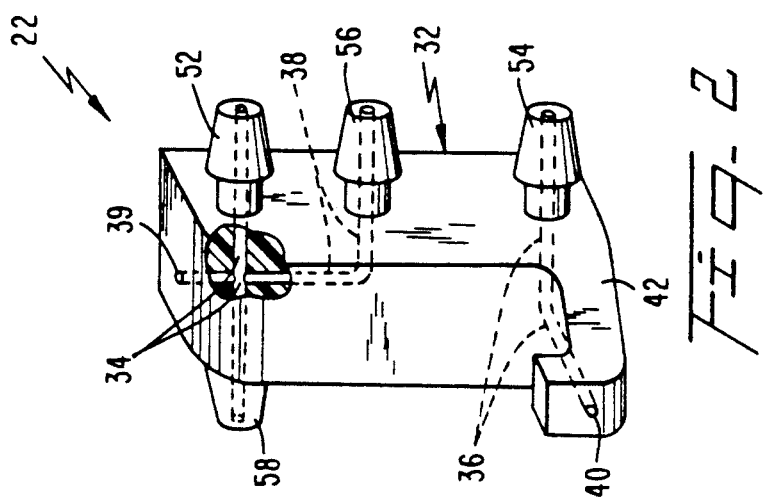
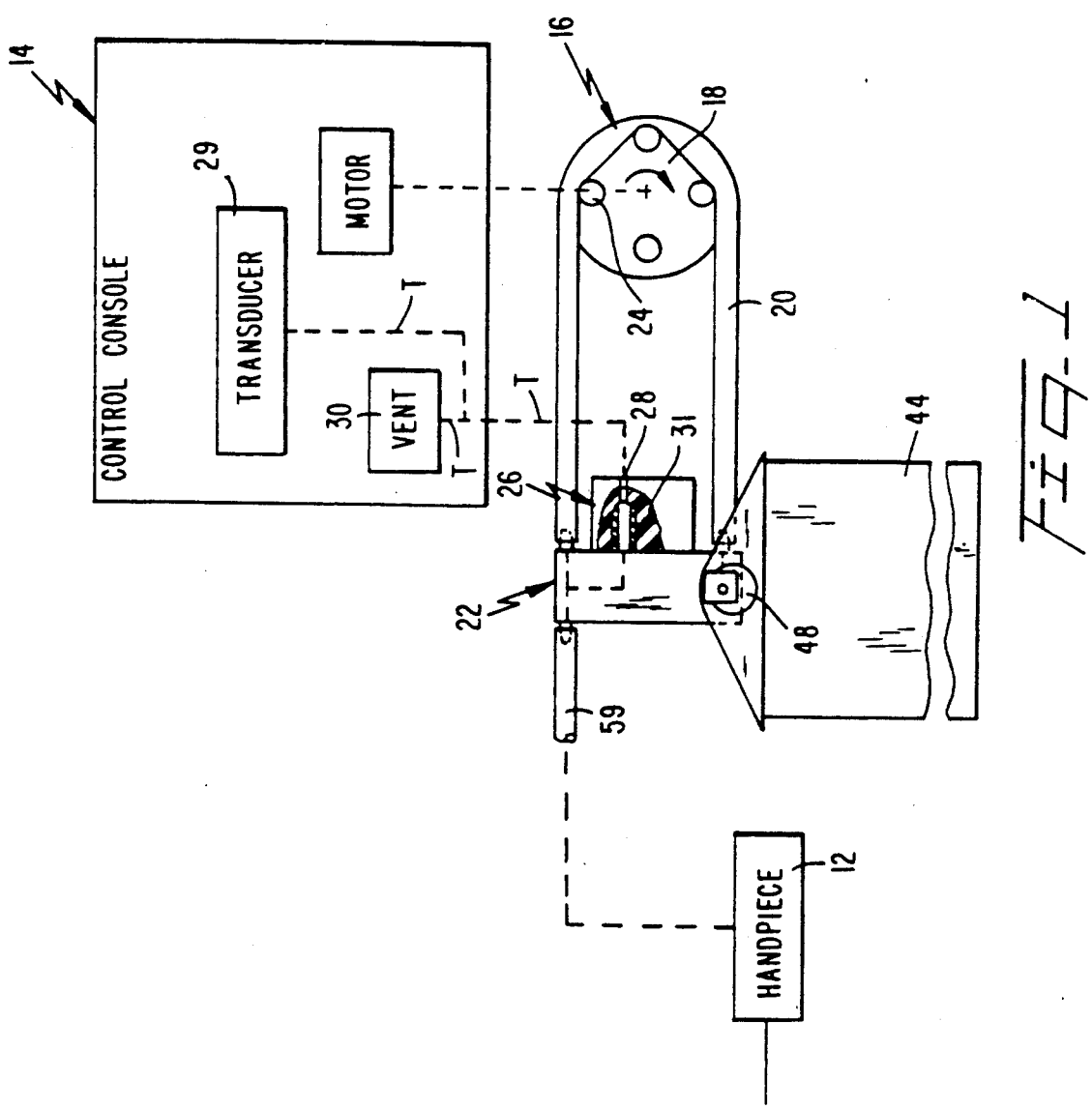

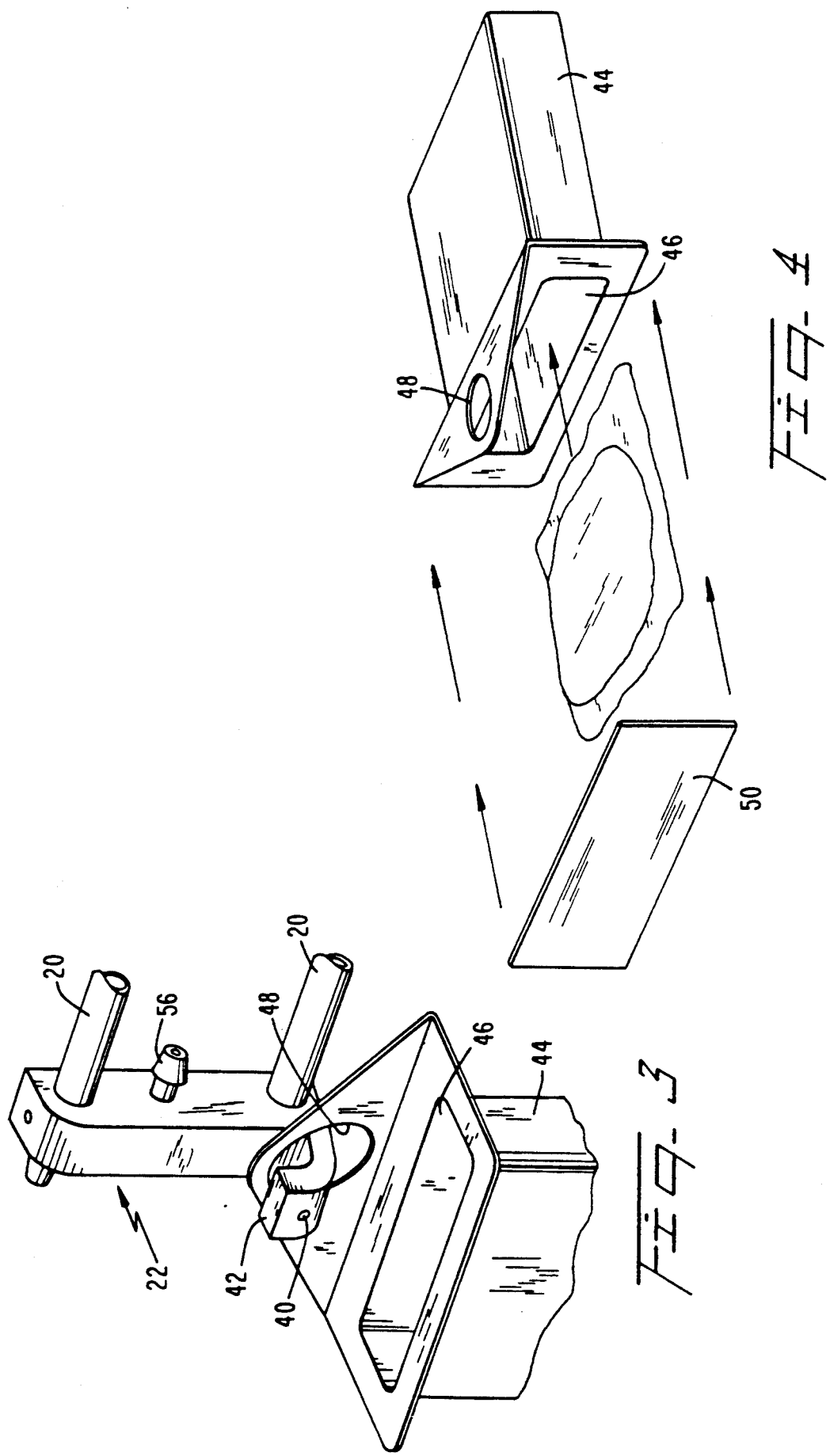

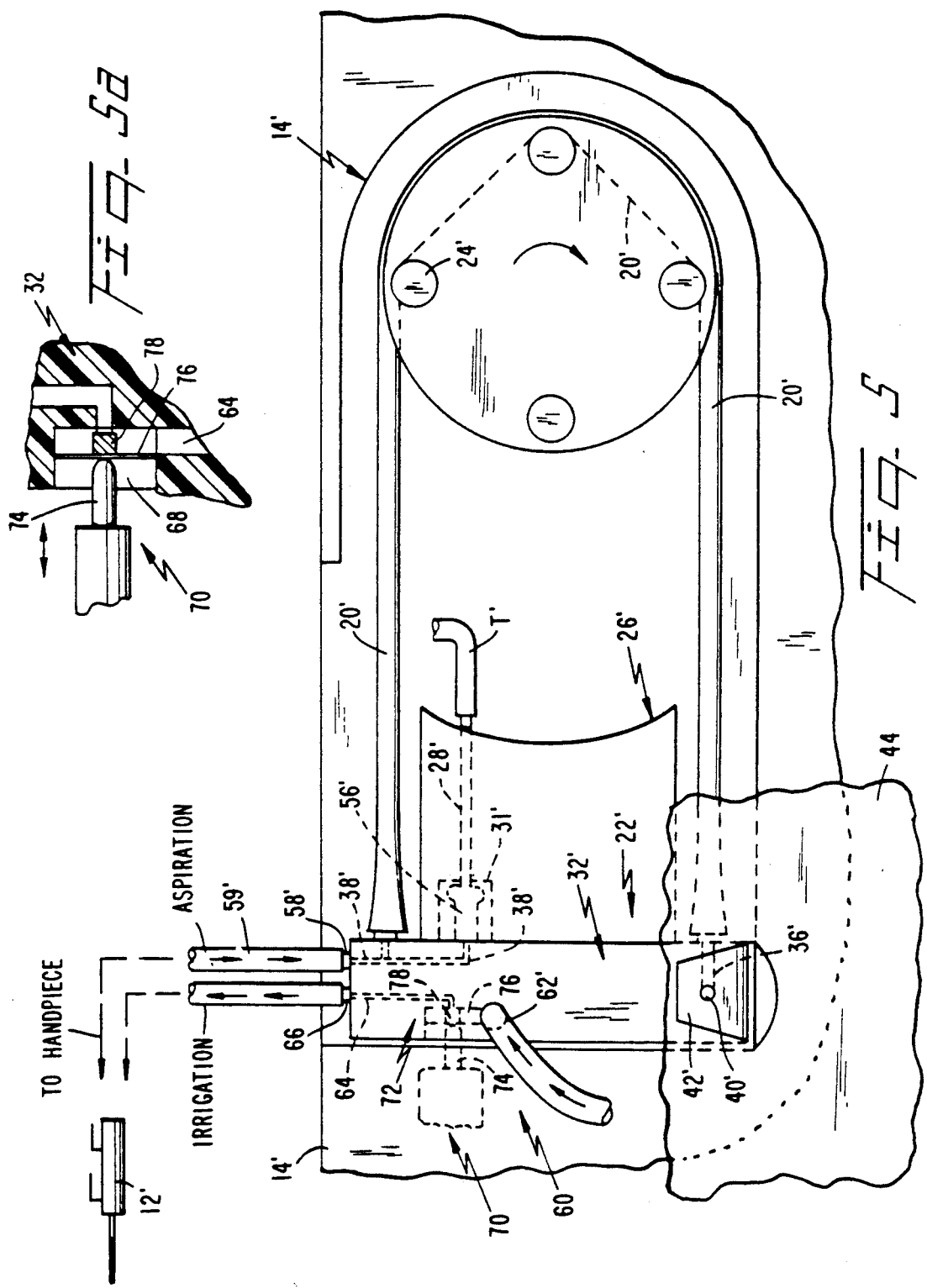

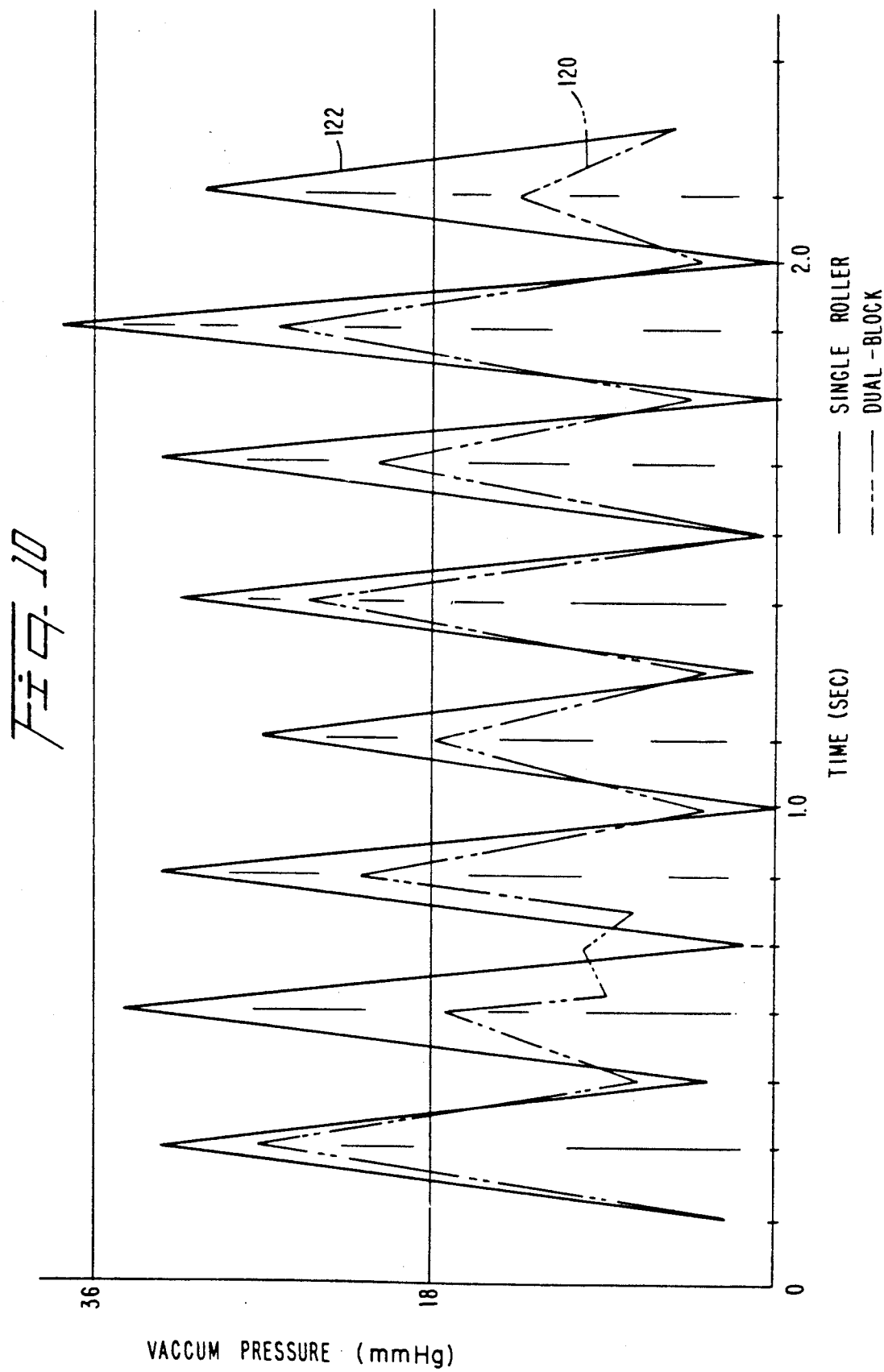

FLUID HANDLING METHOD AND SYSTEM AND FLUID INTERFACE APPARATUS USABLE THEREWITH

BACKGROUND OF THE INVENTION

The present invention relates generally to a fluid handling method and system for use in microsurgical applications and, more particularly, to such a method and system which minimizes fluid pressure of a peristaltic type pumping system. The system incorporates an improved fluid interface apparatus that greatly facilitates coupling of system components at the surgical site.

Microsurgical systems have gained widespread acceptance because they perform precise and minimum invasive surgery. One kind of system is a phacoemulsification type irrigation/aspiration system for use in ophthalmic surgery. Typically, in such a system, there is provided a microsurgical handpiece which is a small handheld device that can selectively remove body tissue with great control. The handpiece fragments the tissue, which tissue is then aspirated from the surgical site by an aspiration conduit to a suitable collection vessel. The suction produced in aspiration is controlled by an irrigation/aspiration control unit. Such unit also controls irrigation or infusion to the operative site.

As concerns aspiration, a peristaltic pumping system is often used for providing the necessary negative pressure. Peristaltic pumping systems offer numerous advantages in such kinds of surgery. For instance, they enhance fluid control, simplify venting and the aspirated fluids do not have the potential for contaminating pump components. While peristaltic type pumping systems provide numerous advantages there are nevertheless certain trade offs. One notable trade off is when such pumps are used, in for example ophthalmic procedures, there results eye turbulence (e.g., iris flutter). Attempts have been made to overcome such turbulence. Some of them utilize added and costly components to the control system. Consequently, there is an ongoing interest in providing effective and less costly devices to minimize pressure pulsations using a peristaltic pumping arrangement.

Also included in these fluid handling systems are a fluid control unit and fluid circuit elements, such as tubing, for use in interconnecting the microsurgical handpiece to the control unit. In using these components it is advantageous to insure correct, easy and reliable fluid connections as well minimize the number of components used when setting up for a procedure at the operative site. Accordingly, there is an ongoing interest in improving such setting-up procedures, by easy to use and reliable components.

SUMMARY OF THE INVENTION

In accordance with the present invention there is provided a fluid handling system for use in controlling aspiration of tissue and fluid from a surgical site through a surgical handpiece having an aspiration passage. The system comprises a control means including peristaltic pumping means being operable for aspirating body tissue and fluid from the site through the handpiece passage. Provision is made for a fluid interface means fluidly coupled to and between the handpiece and the pumping means. The fluid interface defines passage means for allowing aspiration of fluid from the handpiece to the pumping means. Included in the pumping means is at least a pair of rotatable head assemblies, each being mounted for rotational movement. Fluid conduits are provided with each being coupled to a respective one of the head assemblies and fluidly coupled to the passage means for allowing aspiration therethrough in response to operation of the head assemblies. The head assemblies being arranged with respect to each other so that the combined pumping pulsations produced by them and experienced at the surgical site are diminished relative to the individual pulsations generated by each of the head assemblies alone.

In one illustrated embodiment, the head assemblies are ganged together about a common drive shaft and each have their rollers angularly offset relative to other rollers so as to diminish the fluid pressure pulsations produced by both head assemblies at the surgical site.

It is another object of the present invention to provide an improved fluid handling system for use in controlling aspiration from a surgical site through a surgical handpiece having an aspiration passage. The present invention provides for a system comprising control means including peristaltic pumping means being operable for aspirating body tissue and fluid from the site through the handpiece assembly. Included in the system is a fluid interface mountable on the control and having fluid passage means. Also included is conduit means fluidly coupled to the fluid passage means and being operably connected to the pumping assembly for allowing control of fluid through the passage means from the handpiece in response to operation of the pumping assembly. The pumping assembly includes a peristaltic pump having a rotatable head assembly. The conduit means includes elastomeric tubing mounted on the rotatable head assembly and connected to the interface apparatus in such a manner as to removably secure the interface apparatus to a mounted condition on the control means.

In an illustrated embodiment, the passage means defines a discharge passage with a discharge port. A collection vessel is mountable on the fluid interface apparatus for receiving aspirated material through the discharge port. The collection vessel is sized and shaped to serve as a package for the interface apparatus prior to use as a collection vessel.

In another illustrated embodiment, the interface apparatus includes an infusion passage for allowing infusion fluid to flow from a fluid source to the handpiece. The control mechanism includes a mechanism operable in response to signals for blocking and unblocking the flow of infusion fluid in the interface apparatus.

The present invention also contemplates an improved fluid interface apparatus having the characteristics mentioned above in the fluid handling system.

The present invention also contemplates an improved method for aspirating fluid by reason of reducing the pressure fluctuations associated with peristaltic pumping. The method comprises the step of providing peristaltic pumping means being operable for aspirating body tissue and fluid from the site through the handpiece passage; the step of providing fluid interface means fluidly coupled to and between the handpiece and the pumping means; providing the interface means with passage means for allowing aspiration of fluid from the handpiece to the pumping means; the step of providing a pumping means with at least a pair of rotatable head assemblies, each being mounted for rotational movement; the step of coupling a fluid conduit to a respective one of the head assemblies for allowing aspiration therethrough in response to operation of the head assemblies; and, the step of arranging the head assemblies with respect to each other so that combined pumping pulsations produced by them and experienced at the surgical site are diminished relative to the individual pulsations generated by each of the head assemblies alone.

Among the other objects the features of the present invention are the provision of an improved fluid handling system for use in controlling the flow of fluid to and from a microsurgical handpiece used in microsurgery; the provision of a fluid handling system including plural peristaltic pump head assemblies which are arranged relative to each other for providing dampened pressure pulsations at the handpiece; the provision of a system of the last noted type wherein the pump head assemblies can be angularly adjusted relative to each other for adjusting the degree of pulsation dampening; the provision of a system of the above noted type which improves vacuum rise time and flow rate; the provision of a fluid interface apparatus mountable on the control mechanism of a fluid handling system; the provision of an inexpensive fluid interface which facilitates easy set-up of the fluid circuitry elements to and between the microsurgical device and a control mechanism for use therewith; the provision of a collection vessel in combination with the fluid interface apparatus wherein the collection vessel preliminarily serves as a receptacle for the apparatus; the provision of a fluid handling system including a peristaltic pump and an elastomeric tubing stretched around operative components of the peristaltic pump to urge the interface apparatus into a mounted condition; the provision of the fluid interface apparatus of the above-noted type which includes a transducer port and infusion port and passage; and, the provision of the interface apparatus of the last noted type which includes a sealing member selectively operable for selectively sealing the infusion passage.

BRIEF DESCRIPTION OF THE DRAWINGS

FIG. 1 is a diagrammatic view of an improved fluid handling system of the present invention;

FIG. 2 is a perspective view illustrating a fluid apparatus of the present invention;

FIG. 3 is a somewhat enlarged and fragmented diagrammatic representation of certain components of the present invention;

FIG. 4 is an exploded perspective view of another aspect of the present invention;

FIG. 5 is a schematic representation of another embodiment of the present invention;

FIG. 5a is an enlarged and fragmented partly cross-sectional view of a detail of one embodiment of the present invention;

FIG. 10 is a comparison plot showing the displacement of fluid pressure pulsations employing the present invention as opposed to use of a single peristaltic pump.

DETAILED DESCRIPTION

Figure 8:
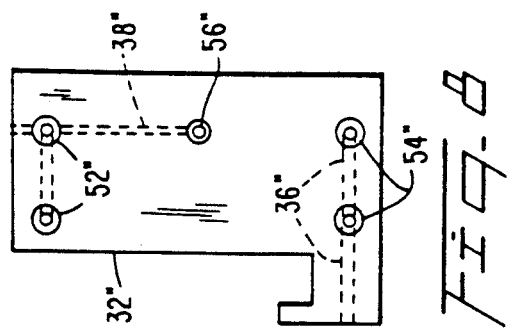
FIG. 8 is a side elevational view of an improved fluidic block of the present invention.
Figure 9:
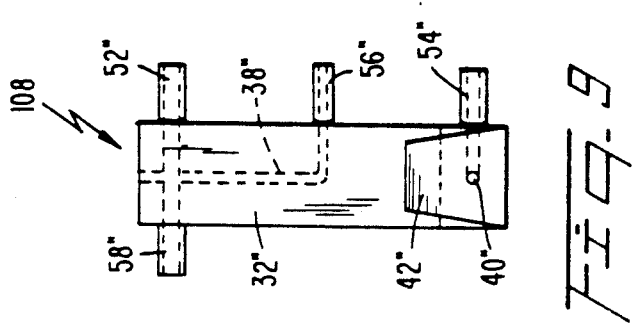
FIG. 9 is a front elevational view of the block shown in FIG. 8.

FIGS. 1-4 relate to one preferred embodiment of a fluid handling system 10 embodying the principles of the present invention. Included in the fluid handling system 10 is a surgical tool or aspiration handpiece 12 which is constructed to remove various kinds of body fluids and tissue. The handpieces to be used in conjunction with the present invention can vary. For instance, the handpiece can be a surgical aspirator cannula, such as described in U.S. Pat. No. 4,784,649 or an ultrasonic surgical aspirator handpiece like that described in U.S. Pat. No. 4,425,115. In this embodiment, the aspirator cannula is to be used as the handpiece 12 and, therefore, irrigating fluid is not required. Since the ultrasonic surgical cannula 12 is known and does not, per se, form an aspect of the present invention a detailed description is not presented herein, but the above-noted aspirator cannula patent is incorporated herein by reference for a detailed description thereof.

The control console 14 can control the flow of irrigation fluid to and aspiration of removed body tissue and fluid from a handpiece as well as controls the supply of power to an ultrasonically operated handpiece if one is to be used, such as described in U.S. Pat. No. 4,425,115. However, in this embodiment only the aspirator control will be discussed, since the handpiece 12 used is the aspirator cannula. Several control consoles are contemplated for use. In this embodiment, the control console 14 is the STTM/C console, which has been modified to include an external peristaltic pump system 16, such as the 9001 peristaltic pump system along with a transducer interface to be described. The STTM/C console and the 9001 pump system are both commercially available from Alcon Laboratories of Fort Worth, Tex. Since the control console does not, per se, form an aspect of this invention a detailed description thereof will be dispensed with.

With continued reference to FIG. 1, since the peristaltic pump system 16 is a known kind only those aspects thereof necessary to understand the invention will be given. The system 16 includes a roller hub assembly 18 which is arranged to protrude forwardly from the front of the control console 14 and be rotatably driven by a suitable motor in the console. Elastomeric aspiration tubing 20, such as silicone, is suitably mounted over the roller hub assembly 18 and is fluidly connected to a disposable fluid interface apparatus 22. Operation of the control console 14 causes the motor to rotatably drive a plurality of equidistant and circumferentially spaced compression rollers 24 on the hub assembly 18. This action results in the sequential compression of the stationary occludable tubing 20 for effecting the desired pumping in a well-known manner.

Referring back to the control console 14, it includes a vacuum transducer interface device 26 (FIG. 2) which has an opening 28 leading to a known kind of vacuum transducer 29 in the console 14 by external tubing T. The transducer 29 serves to monitor and control the vacuum level in the handpiece 12. The interface device 26 is attached to the console 14 and is fluidly coupled to the transducer 29 and an air vent 30. In this regard, the transducer 29 can operate in known manner to open the air vent 30 which leads to the handpiece 12 by tubing T to relieve excess vacuum. The vacuum transducer opening 28 is provided with a rubber grommet 31 which is constructed and sized to releasably cooperate with the fluid interface apparatus 22 in a manner which will be described.

Reference is now made to FIG. 2, for showing the fluid interface apparatus 22 which includes a fluidic interface block 32 that is made of a rigid, low-cost, and moldable plastic material that is intended to be disposable. The fluidic block 32 has a generally elongated shape and is formed with upper and lower aspiration passages 34, 36; respectively, as well as vacuum transducer passages 38. A plug 39 seals the aspiration passages 34. The lower aspiration passages 36 define the fluid discharge extending in the lower extremity of the fluid block 32 and terminating at a discharge port 40. The aspiration passages 34, 36 can have the size and orientation as shown in the drawings although others are contemplated. The fluidic block 32 includes a laterally extending hook-like retaining portion 42 which protrudes forwardly and upwardly so that a fluid/tissue collection vessel 44 may be removably suspended therefrom.

As seen in FIGS. 3 and 4, the collection vessel 44 of this embodiment is, preferably, defined by a semi-rigid and generally parallelpiped plastic receptacle having an opening 46 formed at one end thereof. However, the collection vessel 44 can be made from a variety of materials and is sized to accommodate, for example. 500 ml of aspirated body tissue and fluid. A mounting opening 48 is formed in an upstanding hanger portion which facilitates hanging from the retaining portion 42. In this manner, the aspirant from the discharge port 40 falls into the collection vessel 44. The present invention contemplates that the collection vessel 44 can also preliminarily serve as a package for purposes of packaging and shipping the fluidic interface block 32 and other components including tubing to be used at the operative site. The package includes a plastic lid 50 which is suitably sealed to cover the opening 46. The lid 50 is subsequently removed so that the contents of the package can be removed for use. Prior to use, however, the package can be sterilized by known techniques.

Referring back to the fluidic interface block 32, it has extending from one side thereof a plurality of, schematically depicted, fluid fittings 52, 54, 56 and 58. The fluid fitting 52 is removably secured to one open end of the aspiration tubing 20 while the other end of the aspiration tubing is removably secured to the fluid fitting 54. The fluid fitting 56 is constructed to be removably received in the rubber grommet 31 of the vacuum transducer interface device 26, see FIG. 2. The tubing T, as noted, fluidly couples the interface device 26 to the transducer 29 and vent 30 of the control console 14. Extending from the other side of the fluidic block 32, the fluid fitting 58 is fluidly connected to the aspiration tubing 59 leading from the handpiece 12. In this fashion, tissue from the operative site can be aspirated through the tubing to a suitable collection device (not shown).

After having described the construction of the above embodiment, it is believed its operation is self-evident. To supplement such description, however, it will be appreciated that upon operation of the pumping system 16, the rollers 24 rotate to sequentially compress the aspiration tubing 20 and thereby achieve the desired vacuum for effecting aspiration. In this connection, a slug of fluid is trapped between two rollers which occlude the tubing. As the rollers travel over the stationary tubing 20, the trapped fluid is pushed forward as the leading roller lifts from the tubing. Aspirant from the handpiece 12 is drawn through the tubing 59 to the upper aspiration passages 34, through the tubing 20, the lower aspiration or discharge passages 36 to the discharge port 40 and ultimately into the collection vessel 44.

According to an aspect of the present invention, the fluid interface apparatus 22 is easily mounted on and dismounted from the control console 14. This is significant when the sterilized components are assembled at a surgical site. This is accomplished by coupling or uncoupling the fluidic block 32, by means of the elastomeric aspiration tubing 20, to the roller head assembly 18. As noted, the fluid fitting 56 is removably received in the grommet 31 of the device 26. The longitudinal distance of the transducer device 26 from the roller hub assembly 18 is such that when the interface block 32 is coupled to the transducer device 26, the aspiration tubing 20 is stretched or tensioned. This tensioning serves to urge the fluidic block 32 firmly and releasably against a supporting surface on the vacuum transducer device 26, as shown in FIG. 1. It is contemplated that other structure (not shown) on the control console 14 can also serve to seat the fluidic block 32. Thus, setting up and removal of the fluid interface apparatus 22 is accomplished extremely easily and reliably.

On the other hand if the handpiece were to be an ultrasonic aspirator having irrigating functions, the aspiration control would be achieved as noted above and the irrigating functions would be accomplished in a known fashion using the control console 14 and such handpiece.

Reference is made to FIGS. 5 and 5a for describing another preferred embodiment of the present invention. It should be noted that the structure of this embodiment like that in the previous embodiment will be designated by the same reference numerals with, however, the addition of a prime marking. In this particular embodiment, the fluid interface block assembly 32' is provided with an infusion fluid assembly 60. The interface block assembly 32' is operable with the vacuum transducer device 26' having a suitable rubber grommet 31' that communicates fluidly with a vacuum transducer opening 28'. The transducer opening 28' cooperates with the vacuum transducer and vent of the control console 14' by means of the tubing T'.

The fluid block assembly 32' is provided with a irrigation inlet fitting 62, an irrigation passage generally designated by reference numeral 64, irrigation outlet fitting 66 and a side opening 68. Since the aspiration aspect has been described in the previous embodiment, the following description will concern the irrigation aspects of this embodiment. For selectively controlling the passage of irrigation fluid from a suitable source (not shown) to the handpiece 12', there is provided a selectively operable pinch valve module 70 on the console 14 and a sealing assembly 72 formed in the fluid block assembly 32'. In this embodiment, the handpiece 12' is a surgical aspirator type having irrigating functions, such as in U.S. Pat. No. 4,425,115. The sealing assembly 72 is adapted to fit within the opening 68 or cavity formed in the block assembly 32'. The pinch valve arrangement 70 is a module that has been added to the control console 14'. Specifically, the irrigation pinch valve control normally found in the console 14' has been replaced by the one depicted. The pinch valve module 70 includes a solenoid plunger 74 which is arranged to cooperate with the sealing assembly 72 in a manner to be described. The sealing assembly 72 of this embodiment includes an elastomeric diaphragm sealing member 76 which has a sealing plug member 78 centrally attached thereto which is sized and configured to block or seal the flow of irrigation fluid in the irrigation passage 64. The block opening 68 is cooperably disposed in registration with the solenoid plunger 74. Energization of the solenoid plunger 74, under the control of a procedurist, is effective to displace the diaphragm sealing member 76 inwardly and thereby have the plug 78 occlude the flow of irrigation fluid to the irrigation passage 64. Deenergization of the solenoid, causes plunger retraction, thereby allowing the inherent resiliency of the diaphragm member 76 to return to a non-sealing condition. Also, pressure of the irrigation fluid assists in displacing the diaphragm assembly 76 to its original non-sealing condition. Consequently, irrigation fluid is allowed to flow through the irrigation passage 64 to the handpiece 12 via aspiration fitting 66. The aspiration fitting 66 replaces aspiration fitting 58.

The significance of the foregoing constructions of the fluid apparatus 22, 22' is that they provide for a simplified construction allowing easy and reliable coupling of several fluid tubing members to the control console and the surgical handpiece at the surgical site. Thus, the set-up procedure is not complicated and these embodiments facilitate quick and easy connection of the components and tubing.

Figure 6:
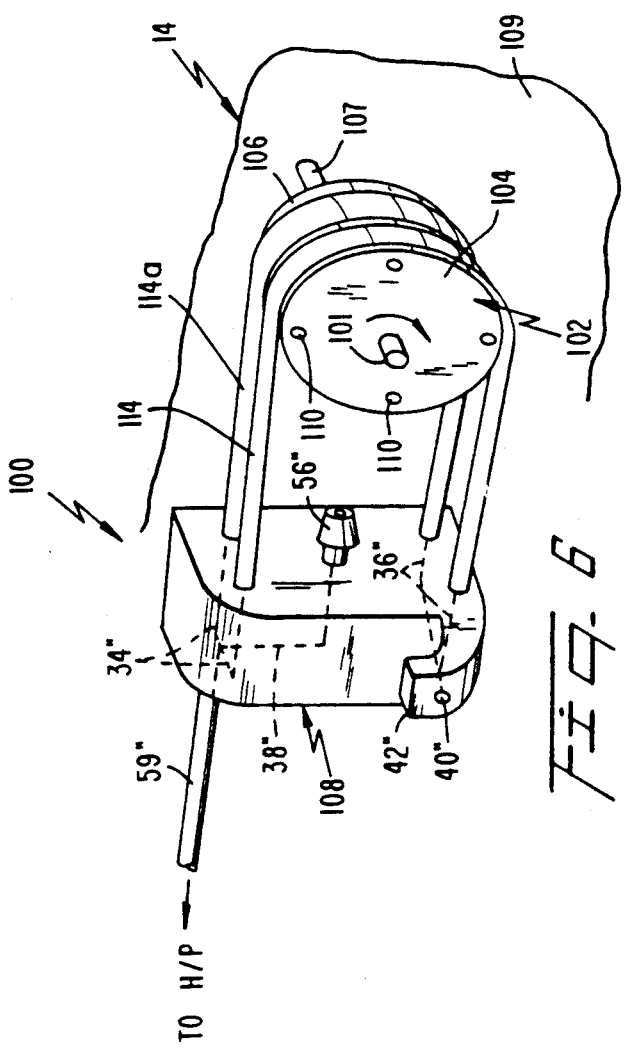
FIG. 6 is a schematic representation of another preferred embodiment of the present invention.

Reference is now made to FIGS. 6-10 for illustrating another preferred embodiment of the present invention. In this embodiment, there is provided a fluidic system 100 for use in reducing fluidic pulsations at the surgical handpiece (not shown), such as the types described above. These pulsations arise of a positive displacement pump, such as a peristaltic pump. In FIG. 6, there is shown a system 102 which includes dual peristaltic roller head assemblies 104 and 106. The roller head assemblies 104, 106, are tandemly mounted for rotation on a common rotational drive shaft 107 extending from a front chassis panel 109 of the control console 14. Both the control console 14 and the pumping system 102 are like the control console and pumping systems of the previous embodiments with the exception that there are a multiplicity of roller head assemblies. For sake of clarity, the vacuum transducer device 26 has been omitted from the drawing of this embodiment.

Included in the fluidic system 100 is a dual fluidic block assembly 108 for use in connecting the plurality of peristaltic pumping assemblies 104, 106 to a common aspiration passage in the handpiece. The block assembly 108 provides great simplification for setting up the various components at the surgical site, especially when several pumping units are to be utilized. The dual block assembly 108 is like the block assembly 32; but with additional fittings for the additional tubing connected thereto. For simplification in describing the block assembly 108 of this embodiment, the structure thereof that is like the structure of the first embodiment will be indicated by the same reference numeral but with the addition of a double prime marking.

Figure 7:
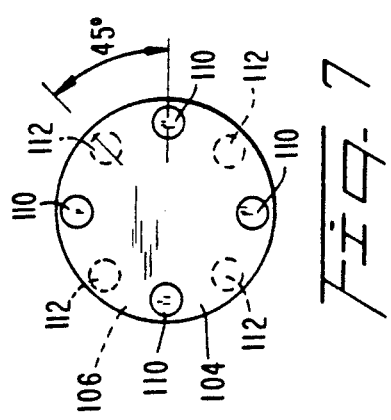
FIG. 7 is a schematic representation illustrating the relative positions of the rollers on the dual roller head assembly.

Each of the roller head assemblies 104, 106 includes a plurality of circumferentially spaced rollers 110, 112; respectively. The rollers 110, 112, are respectively adapted to selectively engage and occlude adjacent silicone tubing 114, 114a. The rollers on each head assembly are spaced at about 90° to the rollers on the same assembly (FIG. 7). However, the rollers 110 on the head assembly 104 are, as shown in FIG. 7, angularly offset vis-a-vis the rollers 112 of the adjacent pump head assembly 106. As will be explained, this is significant in terms of dampening or reducing the amplitude of pumping pulsations of the peristaltic pump system 102 compared to a single roller head assembly.

A motor (not shown) in the console 14 drives both the roller head assemblies 104, 106 so that the rollers 110, 112 contained thereby can sequentially occlude the silicone tubing 114', 114a mounted around the roller head assemblies 104, 106 as depicted. Accordingly, rotation of the roller head assemblies 104, 106 will pump liquid from the surgical site, through the handpiece, the dual fluidic block assembly 108 and into a suitable collection vessel (not shown). As noted, the positioning of the roller head assemblies 104, 106 is angularly displaced relative to each other. This displacement angle allows for adjustment of the degree of pulsation dampening. The displacement angle between the rollers 110, 112 can be adjusted between 0°-90°. It will be understood that at the displacement angles 0° and 90° no pulsation reduction occurs. In this invention, it is preferred that one set of rollers 112 are displaced behind the other set of rollers 110 by about 45°. This provides for optimum reduction of pulsations when both head assemblies are simultaneously rotated. It will be understood that with peristaltic pumps, a slug of fluid is trapped between the two rollers of the same head as they occlude the tubing. As the rollers travel over the tubing, the trapped fluid is pushed forward as the leading roller lifts from the tubing. However, when the leading roller initially occludes the tubing before the trailing roller of the same roller head assembly occludes, there results a pulse or surge of fluid that travels back toward the surgical site. This results in, for example, eye turbulence. It has been determined that by having the rollers 110 angularly offset relative to the rollers 112, as noted above, the pulsations at the handpiece, by the combined pumping of the roller head assemblies 104, 106 are diminished significantly when compared to the pulsation values of a single roller head assembly. FIG. 10 shows plots 120, 122 of the peak displacements of a system using dual pumps as contrasted a single pump system; respectively.

The fluidic cancellation of pulsations is achieved when for instance a roller 110 on, for example, the pump head assembly 104 is generating a pulse cycle (i.e., the fluid travels backwards to the handpiece) while the other roller 112 has started its vacuum cycle (i.e., the fluid is pulled from the handpiece). This cooperation reduces the intensity of fluidic pulsations at the handpiece. With continued reference to FIG. 10, when the dual pumps are running, at a measured fluid output of, for example, 23 cc/min, and the rollers are offset by 45°, the difference in pulsation amplitude (peak-to-peak displacement) is reduced 45%. In this system, the frequency rate of the pulsation peaks is the same whether for a single line system or the dual pump system. From the foregoing description it is believed that operation of this embodiment is self-evident.

Other significant advantages accrue by virtue of the foregoing arrangement. It has been found that with the number of rollers increased (i.e., 4 vs. 8) the dual pumps need run at half the speed of a single line system. Therefore, the flow rate can be doubled to any given pump head rpm. As the vacuum rise time is a function of flow rate and system fluidic resistance, it will be understood that by increasing the flow rate there will be a reduction in the vacuum rise time. While the benefits of reducing pulsations in a surgical handpiece have been described in the context of a peristaltic pump arrangement, this invention contemplates use of other positive-displacement pumps, using for example piston pumps, which are timed to cooperate in a manner which reduces the combined pulsations thereof.

Since certain changes may be made in the above-described methods, system and apparatus without departing from the scope of the invention herein involved, it is intended that all matter contained in the description or shown in the accompanying drawings shall be interpreted as illustrative and not in a limiting sense.

What is claimed is:

1. A fluid handling system for use in controlling aspiration of tissue and fluid from a surgical site through a surgical handpiece having an aspiration passage, said system comprising:

control means including a peristaltic pumping means being operable for aspirating body tissue and fluid from the site through the handpiece passage;

fluid interface means fluidly coupled to and between said handpiece and said pumping means, said interface means defining passage means for allowing aspiration of fluid from the handpiece to said pumping means; and, said pumping means including at least a pair of rotatable head assemblies wherein each one of said head assemblies includes at least one roller, each of said head assemblies being mounted for rotational movement, and fluid conduits each being coupled to a respective one of said head assemblies and fluidly coupled to said passage means for allowing aspiration through the handpiece passage, said passage means and said conduits in response to operation of said head assemblies, said head assemblies being operably arranged with respect to each other wherein said rollers of said one head assembly is offset angularly with respect to said roller of the other head assembly so that during rotational movement thereof that the combined pumping pulsations produced by them and experienced at the surgical site are diminished relative to the individual pulsations generated by each of said head assemblies pumping alone.

2. The system of claim 1 wherein said head assemblies are arranged to rotate about a common rotational axis.

3. The system of claim 1 wherein each of said head assemblies is provided with a plurality of rollers and wherein said rollers of one of said head assemblies are angularly displaced relative to said rollers of the other of said head assemblies.

4. The system of claim 3 wherein said angular displacement can range from between 0 to 90 degrees.

5. The system of claim 4 wherein said rollers are angularly displaced by about 45 degrees.

6. The system of claim 1 wherein said interface means is removably secured to said control means.

7. The system of claim 6 wherein each of said conduit is an elastomeric tubing releasably mounted on each of said rotatable head assemblies by releasable tensioning thereof so as to removable secure said interface means against a mounting surface on said control means.

8. The system of claim 4 wherein said head assemblies are arranged to reduce pulsations by about up to 45%.

9. The system of claim 8 further including a collection vessel removably mountable on said fluid interface means for receiving material through a discharge port defined by a discharge passage in said passage means.

10. The system of claim 9 wherein said interface means includes a supporting portion extending therefrom and through which said discharge passage extends.

11. The system of claim 9 wherein said collection vessel is a drainage bag constructed to be removably mounted on said supporting portion and having an opening communicable with said discharge port.

12. The system of claim 11 wherein said collection vessel is sized and shaped to serve as part of a package prior to use as a collection vessel wherein said vessel can store said interface means.

13. The system of claim 1 wherein said interface means includes vacuum transducer port means fluidly communicating with said passage means and removably cooperable with a vacuum transducer opening of said control means.

14. The system of claim 1 wherein said interface means includes infusion passage means for allowing infusion fluid to flow from a fluid source to the handpiece.

15. The system of claim 14 wherein said interface means includes occluding means mountable in an opening in said apparatus and being operable between occluding and non-occluding positions.

16. A fluid handling system for use in controlling fluid flow relative to a surgical handpiece used in microsurgery, said system comprising:

a control mechanism including a pumping assembly;

a fluid interface apparatus mountable on said control mechanism and having fluid passage means;

conduit means fluidly coupled to said fluid passage means and being operably connected to said pumping assembly for allowing control of fluid through said passage means from the handpiece in response to operation of said pumping assembly; and, said pumping assembly including a peristaltic pump having a rotatable head assembly, and said conduit means including elastomeric tubing releasably mounted on said rotatable head assembly by releasable tensioning thereof so as to removably secure said interface apparatus against a mounting surface on said control mechanism.

17. The system of claim 16 wherein said passage means defines a discharge passage with a discharge port.

18. The system of claim 17 further including a collection vessel removably mountable on said fluid interface apparatus for receiving material through said discharge port.

19. The system of claim 18 wherein said interface apparatus includes a supporting portion extending therefrom and through which said discharge passage extends.

20. The system of claim 18 wherein said collection vessel is a drainage bag removably mounted on said supporting portion and having an opening therein communicable with said discharge port.

21. The system of claim 20 wherein said collection vessel is sized and shaped to serve as part of a package prior to use as a collection vessel.

22. The system of claim 21 wherein said interface apparatus includes vacuum transducer port means for fluidly communicating with said passage means wherein said passage means defines a transducer passage, said transducer port means communicating with a vacuum transducer opening of said control mechanism.

23. The system of claim 16 wherein said interface apparatus includes infusion passage means for allowing infusion fluid to flow from a fluid source to the handpiece.

24. The system of claim 23 wherein said interface apparatus includes occluding means cooperating with said infusion passage means and is movable between occluding and non-occluding positions.

25. The system of claim 24 wherein said occluding means includes a diaphragm member secured to an opening in said interface apparatus and being movable between said occluding and non-occluding conditions.

26. A fluid handling system for use in controlling fluid flow from a surgical handpiece having an aspiration passage, said system comprising:
control means including positive displacement pumping means being operable for aspirating body tissue and fluid from the site through the handpiece passages;
fluid passage means for allowing aspiration of fluid from the handpiece to said pumping means; and,
said pumping means being coupled to said passage means for allowing aspiration therethrough in response to operation of said displacement pumping means, said pumping means inclining at least two positive pumping arrangements each one of which produces pumping pulsations and each being operably arranged with respect to each other so that during operation thereof the combined pumping pulsations produced by each of said arrangements and experienced at the surgical site are diminished relative to the individual pulsations generated by each of said arrangements pumping alone.

27. The system of claim 26 wherein said pumping arrangements are peristaltic pumping arrangements.

28. A method for use in controlling aspiration of tissue and fluid from a surgical site through a surgical handpiece having an aspiration passage, said method comprising the steps of:
providing peristaltic pumping means being operable for aspirating body tissue and fluid from the site through the handpiece passage;
providing fluid interface means fluidly coupled to and between the handpiece and the pumping means;
providing the interface means with passage means for allowing aspiration of fluid from the handpiece to the pumping means;
providing the pumping means with at least a pair of rotatable head assemblies;
coupling a fluid conduit to a respective one of the head assemblies for allowing aspiration through the conduit in response to operation of the head assemblies; and,
arranging the head assemblies with respect to each other so that when operating the combined pumping pulsations produced by them and experienced at the surgical site are diminished relative to the individual pulsations generated by each of the head assemblies alone.

29. The method of claim 28 wherein said arranging of the pump head assemblies is done so that they rotate about a common rotational axis.

30. The method of claim 29 wherein said step of providing the head assemblies includes providing each with a plurality of rollers and wherein said arranging of the head assemblies includes arranging the rollers of one of the head assemblies to be angularly displaced relative to the rollers of the other of the head assemblies so as to diminish pumping pulsations.

31. The method of claim 30 wherein said step of angularly displacing the rollers is done in a range from between 0 to 90 degrees.

32. The method of claim 31 wherein said step of angularly displacing the rollers is done so that they are about 45 degrees displaced relative to each other.

33. An apparatus for use with a fluid handling system including a control mechanism including a peristaltic pumping assembly having a rotatable head assembly used for controlling fluid flow relative to a surgical handpiece used in microsurgery, said apparatus comprising:
a fluid interface apparatus mountable on said control mechanism and having fluid passage means;
conduit means fluidly coupled to said fluid passage means and being operably connected to the pumping assembly for allowing control of fluid through said passage means from the handpiece in response to operation of the pumping assembly; and,
said conduit means including elastomeric tubing releasably mountable on the rotatable head assembly by releasable tensioning thereof so as to facilitate removably securing said interface apparatus against a mounting surface on the control mechanism.

34. The apparatus of claim 33 wherein said passage means defines a discharge passage with a discharge port.

35. The apparatus of claim 34 further including a collection vessel removably mountable on said fluid interface apparatus for receiving material through said discharge port.

36. The apparatus of claim 35 wherein said interface apparatus includes a supporting portion extending therefrom and through which said discharge passage extends.

37. The apparatus of claim 36 wherein said collection vessel is a drainage bag removably mounted on said supporting portion and having an opening therein communicable with said discharge port.

38. The apparatus of claim 37 wherein said collection vessel is sized and shaped to serve as part of a package prior to use as a collection vessel.

39. The apparatus of claim 33 wherein said interface apparatus includes infusion passage means for allowing infusion fluid to flow from a fluid source to the handpiece.

40. The apparatus of claim 39 wherein said interface apparatus includes occluding means cooperating with said infusion passage means and is movable between occluding and non-occluding positions.

41. The apparatus of claim 40 wherein said occluding means includes a diaphragm member secured to an opening in said interface apparatus and being movable between said occluding and non-occluding conditions.

42. The apparatus of claim 33 wherein said passage means connects fluidly a plurality of conduits of said conduit means from a plurality of pumps to at least a single handpiece passage.

43. The apparatus of claim 42 wherein said interface apparatus includes a block member made of a moldable plastic material.

44. A fluid handling assembly for use in controlling fluid flow between a control mechanism having a mounting surface and a surgical handpiece used in microsurgery, said assembly comprising:
a fluid interface apparatus mountable on the mounting surface of the control mechanism and having fluid passage means for allowing passage of fluid; and conduit means fluidly couplable to said fluid passage means and being operably connectable to the control mechanism for allowing control of fluid through said passage means and said conduit means including elastomeric tubing releasable mountable on the control mechanism by releasable tensioning thereof so as to removably secure said interface apparatus against the mounting surface on the control mechanism.

45. The system of claim 44 wherein said passage means defines a discharge passage with a discharge port, and a collection vessel removably mountable on said fluid interface apparatus for receiving material through said discharge port.

46. The assembly of claim 45 wherein said interface apparatus includes a supporting portion extending therefrom and through which said discharge passage extends.

47. The assembly of claim 46 wherein said collection vessel is a drainage bag removably mounted on said supporting portion and having an opening therein communicable with said discharge port.

48. The apparatus of claim 47 wherein said collection vessel is sized and shaped to serve as part of a package prior to use as a collection vessel.

49. The apparatus of claim 44 wherein said interface apparatus is disposable.

50. The system of claim 44 wherein said interface apparatus includes vacuum transducer port means for fluidly communicating with said passage means wherein said passage means defines a transducer passage, said transducer port means communicating with a vacuum transducer opening of the control mechanism.

51. The system of claim 44 wherein said interface apparatus includes infusion passage means for allowing infusion fluid to flow from a fluid source to the handpiece.

52. The system of claim 51 wherein said interface apparatus includes occluding means cooperating with said infusion passage means and is movable between occluding and non-occluding positions.

53. The system of claim 52 wherein said occluding means includes a diaphragm member secured to an opening in said interface apparatus and being movable between said occluding and non-occluding conditions.

* * * * *

UNITED STATES PATENT AND TRADEMARK OFFICE
CERTIFICATE OF CORRECTION

PATENT NO. : 5,041,096

DATED : August 20, 1991

INVENTOR(S) : BEUCHAT ET AL.

It is certified that error appears in the above-identified patent and that said Letters Patent is hereby corrected as shown below:

```
In column 1, line 15, change "minimum" to --minimumly--.
In column 1, line 22, delete "tissue" (second occurrence).
In column 1, line 24, change "in" to --for--.
In column 1, line 37, change "there results" to
    --they can cause--.
In column 2, line 24, insert --means-- before "and".
In column 4, line 57, change "(FIG.2)" to --(FIG.1)--.
In column 7, line 17, change "aspiration" to --irrigation--,
    (both occurrences).
In column 7, line 34, insert --pumping-- before "system".
In column 7, line 47, change "peristaltic pumping" to
    --roller head--.
```

Signed and Sealed this

Eighth Day of November, 1994

Attest:

BRUCE LEHMAN

*Attesting Officer*     Commissioner of Patents and Trademarks